United States Patent [19]
Peralta et al.

[11] Patent Number: 4,459,106
[45] Date of Patent: Jul. 10, 1984

[54] DENTAL APPARATUS

[75] Inventors: Michael Peralta, Ft. Lauderdale; Albert S. Goldstein, Jr., Tamarac; Bruce B. Schwartz, Ft. Lauderdale, all of

[73] Assignee: Fluidic Medical Equipment Co., Dania, Fla.

[21] Appl. No.: 406,335

[22] Filed: Sep. 24, 1982

[51] Int. Cl.³ .................................. A61C 19/02
[52] U.S. Cl. .................................. 433/28; 137/842
[58] Field of Search .................. 433/28; 137/842

[56] References Cited
U.S. PATENT DOCUMENTS 3,817,246 6/1976 Weigl .................. 137/842
4,069,587 1/1978 Pepalta .................. 433/28

Primary Examiner—Robert Peshock
Attorney, Agent, or Firm—Darby & Darby

[57] ABSTRACT

A main valve and separate sensing means are mounted in a housing spaced-apart relation. The main valve is formed with a valve chamber having an inlet port and an outlet port, and the valve comprises a valve seat and a valve member cooperating therewith. The valve member is movable between a closed position in which it engages the seat and blocks flow of fluid from the inlet to the outlet and an open position in which it is spaced apart from the seat and enables such flow. The sensing means includes an exhaust to the atmosphere and exhaust shutoff means actuable for closing the exhaust. The housing and main valve are formed with a passage enabling restricted leakage of fluid from the main chamber to the sensing means for exhaust to the atmosphere when the valve member is in the closed position. The leakage fluid is in communication with the valve member and when pressurized applies a force urging the valve member to the open position. The net cross-sectional area of the valve member exposed to the leakage fluid exceeds the cross-sectional area of the valve member exposed to the fluid in the main chamber. Introduction of pressurized fluid into the main chamber coupled with actuation of the exhaust shutoff means therefore builds up the pressure of the leakage fluid and opens the main valve.

16 Claims, 9 Drawing Figures

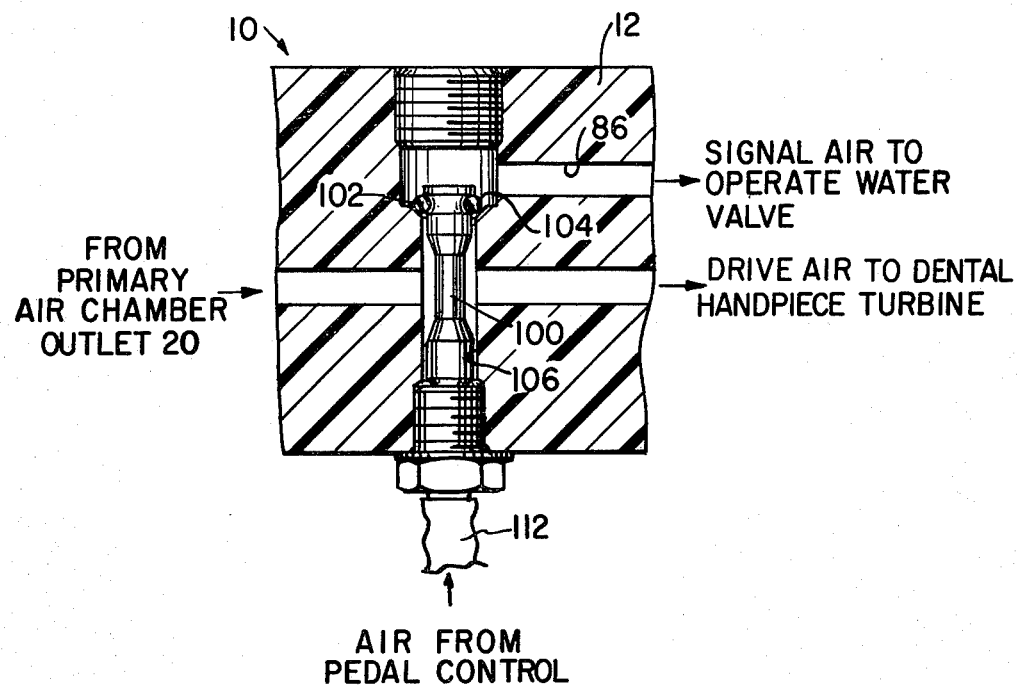

DENTAL APPARATUS

BACKGROUND OF THE INVENTION

This invention relates to apparatus that has a wide range of applications and that is especially adapted for use in dentistry. More particularly, it relates to a novel and highly effective "fluidic block" whereby many power and control functions that have heretofore required bulky, expensive, and complicated equipment can be performed by equipment that is compact, inexpensive and simple.

Modern dentistry requires the use of power tools such as high-speed drills that have the capability of drilling with or without the addition of water, that can be closely controlled as to drill speed and water flow, and that are easy for a dentist to use. Much progress has been made towards providing such tools, including the improvements disclosed in the applicant's prior U.S. Pat. No. 4,069,587.

That patent discloses an arrangement whereby removal of a dental handpiece or tool from its holder coupled with operation of a pedal valve opens a pilot-operated main valve for supplying air or both air and water to the handpiece. The patent discloses several arrangements. In one, there are aligned, narrow air passages on opposite sides of a recess which receives the handpiece, and the handpiece blocks these passages when it is in the holder. Upon removal of the handpiece, the flow of air from one of these passages across the recess and into the the passage supplies pilot pressure enabling opening of the pilot-operated main valve.

The prior structure includes a composite valve that serves both as a main valve for enabling or blocking flow of air to the drill and as the pilot valve for controlling the operation of the main valve. This structure does not lend itself to miniaturization or to the most efficient mass production.

SUMMARY OF THE INVENTION

An object of the invention is to remedy the problems of the prior art and, in particular, to provide apparatus that is easily miniaturized and mass produced. Another object of the invention is to provide apparatus that is easy for a dentist to use and that is simple and reliable.

These and other objects are attained by the provision of apparatus comprising housing means, a main valve mounted in the housing means, and separate sensing means mounted in the housing means in spaced-apart relation to the main valve. The main valve is formed with a main valve chamber having an inlet port and an outlet port, and the main valve comprises a valve seat and a valve member cooperating therewith. The valve member is movable between a closed position in which it engages the seat and blocks flow of fluid from the inlet to the outlet and an open position in which it is spaced apart from the seat and enables such flow.

The sensing means includes an exhaust to the atmosphere and exhaust shut-off means actuable for closing the exhaust. The housing and main valve are formed with a passage enabling restricted leakage of fluid from the main valve chamber to the sensing means for exhaust to the atmosphere when the valve member is in the closed position. The leakage fluid is in communication with the valve member and when pressurized applies a force urging the valve member to the open position. The net cross-sectional area of the valve member exposed to the leakage fluid exceeds the net cross-sectional area of the valve member exposed to the fluid in the main chamber.

Introduction of pressurized fluid into the main chamber coupled with actuation of the exhaust shut-off means therefore builds up the pressure of the leakage fluid and opens the main valve.

The apparatus is preferably characterized by a number of additional features, including the following:

The passage mentioned above enabling restricted leakage of fluid extends the length of the valve member.

The main valve further comprises a second valve seat, the valve member being spaced apart from the second valve seat when the main valve is closed and engaging the second valve seat when the main valve is open, whereby fluid passing between the valve member and the first-named valve seat when the main valve is open can exit through the outlet but is prevented from counteracting the valve-opening force applied by the leakage fluid.

The exhaust shut-off means comprises a flexible diaphragm movable between a normal position in which it leaves the exhaust open and a flexed position in which it closes the exhaust. Means such as a source of compressed air and an air passage extending through the housing and communicating with the source is provided for flexing the diaphragm by directing in air stream against it.

The housing is formed with a recess and the air passage communicates with the recess, whereby an obstruction (such as a dental tool) placed in the recess interrupts the air stream and prevents the air stream from flexing the diaphragm.

A fluid-powered dental tool is adapted to be stored in the recess, and tubing means connects the tool to the main valve chamber outlet mentioned above, whereby the tool is powered by the fluid when the main valve is open and the main valve is closed when the tool is stored in the recess.

A water valve is mounted in the housing means in spaced-apart relation to the main valve and the sensing means. The water valve is formed with a water chamber having a water inlet port and a water outlet port, and the water valve comprises a water valve seat and a water valve member cooperating therewith.

The water valve member is movable between a closed position in which it engages the water valve seat and blocks flow of water from the water inlet to the water outlet and an open position in which it is spaced apart from the water valve seat and enables such flow.

AND-gate means is mounted downstream of the first-named outlet and in fluid communication therewith. Fluid-passage means in the housing provides communication between the AND-gate means and the water valve means.

Means is provided for actuating the AND-gate means, whereby a portion of the fluid passing through the main valve chamber outlet is bled through the fluid passage means to the water valve member and applies a force urging the water valve member to the open position. The net cross-sectional area of the water valve member exposed to the fluid bled from the AND-gate means exceeds the net cross-sectional area of the water valve member exposed to the water chamber.

Actuation of the AND-gate means when the main valve is open therefore opens the water valve.

The water valve further comprises a second water valve seat, the water valve member being spaced apart from the second water valve seat when the water valve is closed and engaging the second water valve seat when the water valve is open. Water passing between the water valve member and the first-named water valve seat when the water valve is open can therefore exit through the water valve outlet but is prevented from counter acting the valve-opening force applied by the fluid bled from the AND-gate means.

The AND-gate means comprises a valve member normally preventing bleeding of a portion of the fluid passing through the main valve outlet. Control means is provided for selectively applying air pressure to the last-named valve member, which moves in response thereto to effect such bleeding.

The control comprises a source of compressed air and a pedal for controlling application thereof to the last-named valve member.

Needle valve means is provided for controlling the rate of water flow when the water valve is open. Lockout means mounted in the housing is provided for selectively interrupting the air stream and thus selectively ensuring that the main valve remains closed. The lockout means comprises a two-position manually operable valve, the valve in one position blocking the air passage and in the other position unblocking the air passage.

BRIEF DESCRIPTION OF THE DRAWING

A better understanding of the invention may be gained from a consideration of the following detailed description of the preferred embodiments thereof in conjunction with the appended figures of the drawing, wherein:

FIG. 9 is a diagrammatic sectional view of a portion of the apparatus of FIG. 1 therefore.

DESCRIPTION OF THE PREFERRED EMBODIMENTS

Figure 1:
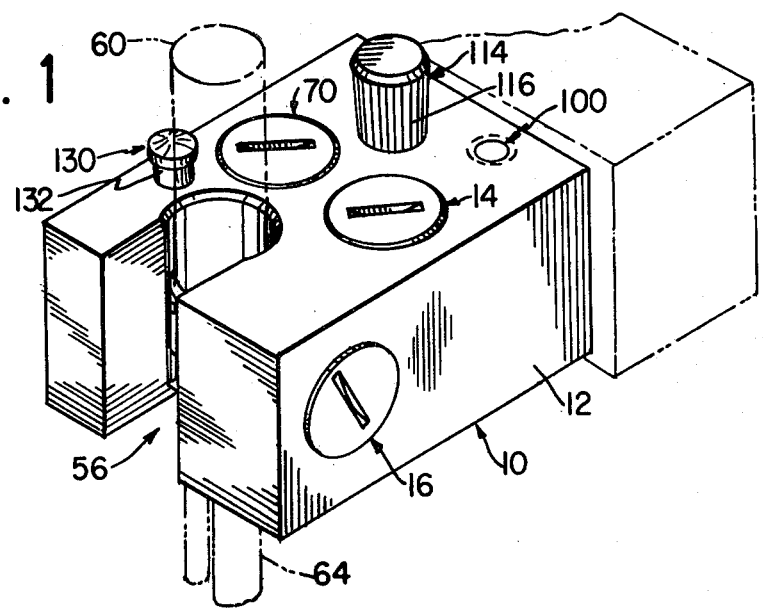
FIG. 1 is a perspective view of apparatus constructed in accordance with the invention.
Figure 2:
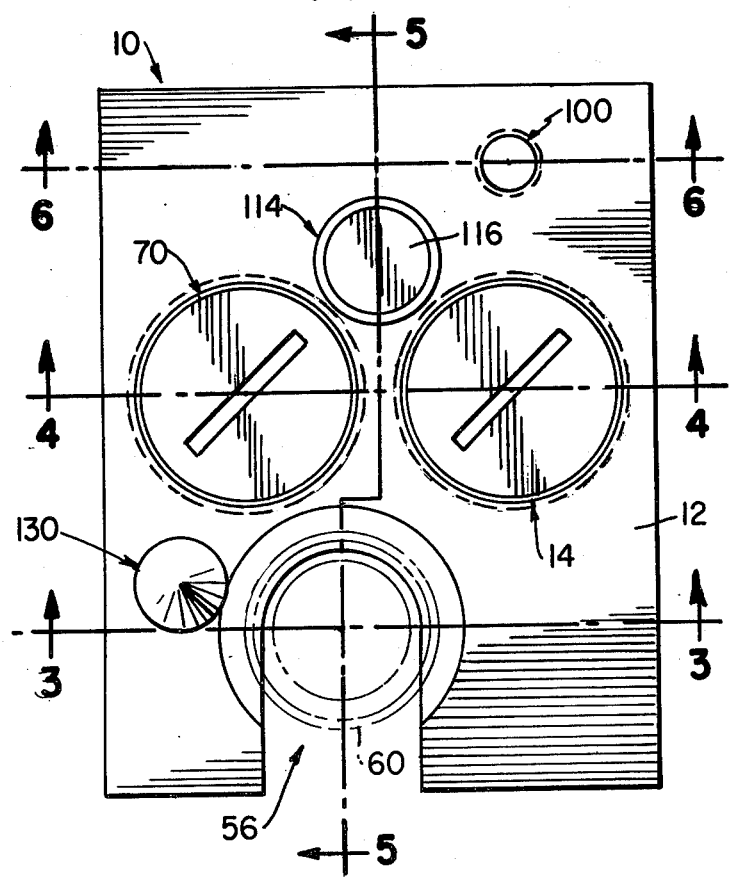
FIG. 2 is a top plan view of the apparatus of FIG. 1.

FIG. 1 shows a "fluidic block" 10 constructed in accordance with the invention. It comprises housing means 12, a main valve 14 mounted in the housing means 12, and separate sensing means 16 mounted in the housing means 12 in spaced-apart relation to the main valve 14.

The main valve 14 is formed with a main valve chamber 17 (FIG. 4) having an inlet port 18 and an outlet port 20, and the main valve 14 comprises a valve seat 22 and a valve member 24 cooperating therewith.

The valve member 24 is movable between a closed position in which it engages the seat 22, preferably by means of an O-ring 26, and blocks flow from the inlet 1B to the outlet 20 and an open position (which is the position shown in FIG. 4) in which it is spaced apart from the seat 22 and enables such flow.

The sensing means 16 (FIGS. 1, 3 and 7) includes an exhaust 28, 29, 30 to the atmosphere and exhaust shut-off means 32 actuable for closing the exhaust 28, 29, 30.

The housing 12 and main valve 14 are formed with a passage 34, 36, 38, 40 (FIGS. 4 and 7) enabling restricted leakage of fluid from the main valve chamber 17 (FIG. 4) to the sensing means 16 for exhaust to the atmosphere through the exhaust 28, 29, 30 when the valve member 24 is in the closed position. The leakage fluid is in communication with the valve member 24 and when pressurized applies a force urging the valve member 24 to the open position illustrated in FIG. 4.

An elastomeric disc seal 42 (FIG. 4) provides a seal with the interior wall 43 of the housing 12 in which the valve member 24 is mounted. The seal 42 is backed up by a plate 44 which provides rigidity. The seal 42 and the plate 44 have a diameter which is larger than that of the portion of the valve member 24 exposed to fluid in the chamber 17.

The net cross-sectional area of the valve member 24 exposed to the leakage fluid is substantially the same as the area of the disc 44. This cross-sectional area exceeds the net cross sectional area of the valve member 24 exposed to the fluid in the main chamber 17. The latter cross-sectional area is substantially equal to the area of a disc having a diameter equal to the diameter of the O-ring 22.

Figure 4:
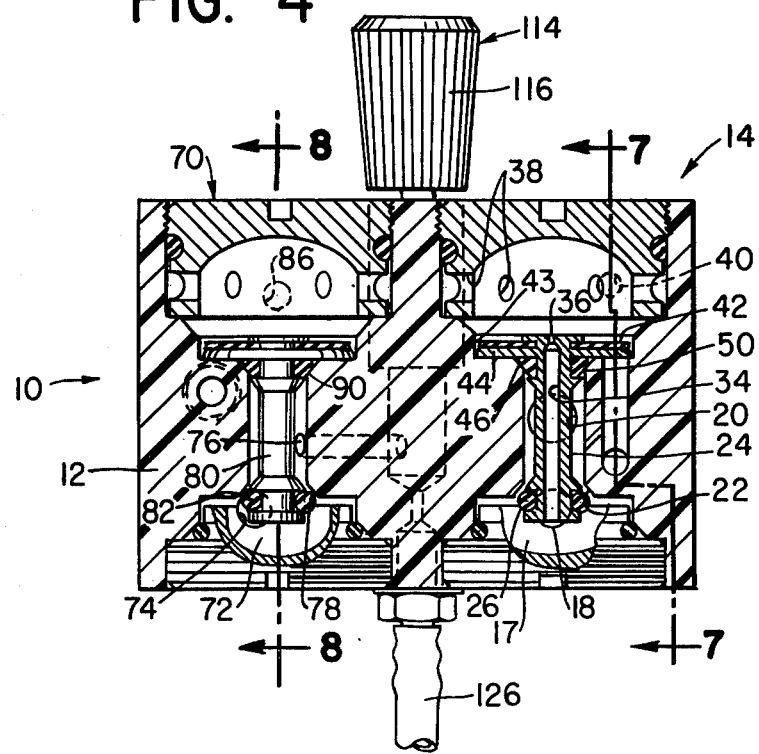
FIG. 4 is a sectional view taken substantially along the lines 4—4 of FIG. 2 and looking in the direction of the arrows.

Since the cross-sectional area of the valve member 24 exposed to the leakage fluid pressure exceeds the cross-sectional area exposed to the pressure of the fluid in the main valve chamber 17, introduction of pressurized fluid into the chamber 17 coupled with actuation of the exhaust shut-off means 32 to shut off the exhaust 28, 29, 30 and build up the pressure of the leakage fluid in the space above the disc 44 forces the valve member 24 to its lower position as illustrated in FIG. 4 and opens the main valve.

The passage 34, 36 extends the length of the valve member 24, as FIG. 4 shows.

The main valve 14 further comprises a second valve seat 46. The valve member 24 is spaced apart from the second valve seat 46 when the main valve 14 is closed and engages the second valve seat 46, as FIG. 4 shows, when the main valve 14 is opened. Accordingly, fluid passing between the valve member 24 and the first-named valve seat 22 when the main valve 24 is open can exit through the outlet 20 but is prevented from counteracting the valve opening force applied by the leakage fluid. Specifically, when the valve 14 is open, the engagement between the O-ring 50 and the valve seat 46 prevents fluid from passing between the main valve member 24 and the valve seat 22 and thus prevents the fluid from acting on the lower face of the plate 44.

Figure 3:
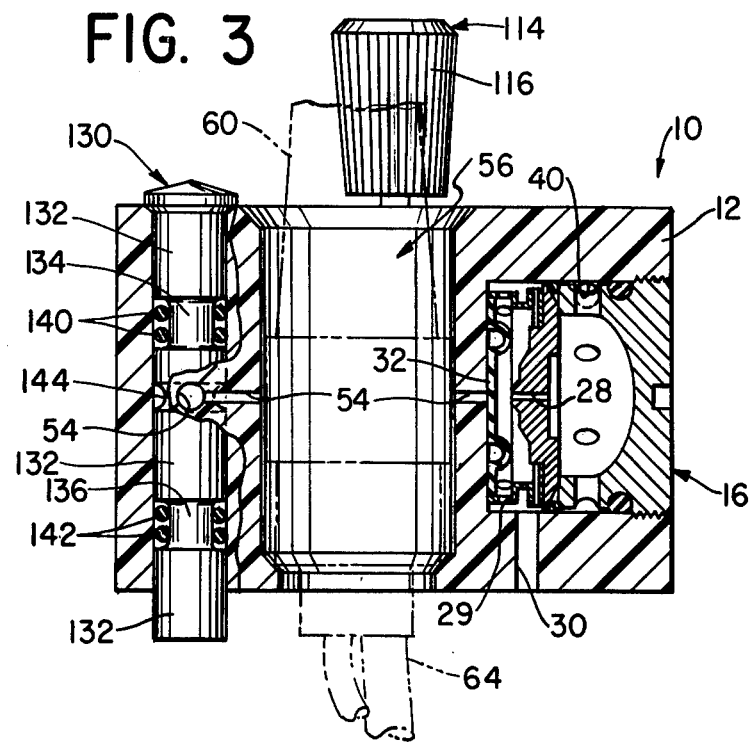
FIG. 3 is a sectional view taken substantially along the lines 3—3 of FIG. 1 and looking in the direction of the arrows.

The exhaust shut-off means 32 (FIG. 3) comprises a flexible diaphragm movable between a normal position illustrated in FIG. 3 in which it leaves the exhaust 28, 29, 30 open and a flexed position in which it closes the exhaust by pressing against the left hand end (as seen in FIG. 3) of the passage 28.

Means is provided for flexing the diaphragm 32. This means comprises a source of compressed air, for example a compressor or tank, and an air passage 54 (FIGS.

3 and 8) extending through the housing 12 and communicating with the source, for directing an air stream against the diaphragm 32. An air line connects the source to the air passage 54. The line includes a pedal control (operated, for example, by the dentist's right foot) and a laminar flow restrictor or air regulator.

Figure 5:
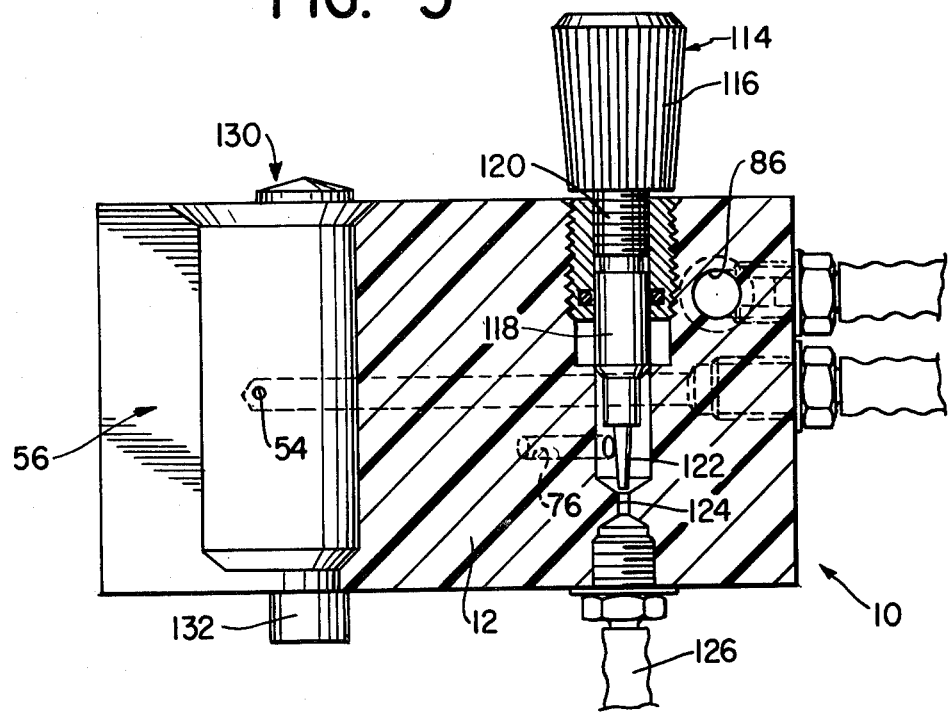
FIG. 5 is a sectional view taken substantially along the discontinuous line 5—5 of FIG. 2 and looking in the direction of the arrows.

The housing 12 is formed with a recess 56 (FIGS. 1, 3 and 5), and the air passage 54 communicates with the recess 56. An obstruction placed in the recess 56 interrupts the air stream across the recess 56 and prevents the air stream from entering the portion of the passage 54 to the right of the recess 56 (as seen in FIG. 3) and flexing the diaphragm 32.

A fluid-powered dental tool 60 (FIGS. 1 and 3) is adapted to be stored in the recess 56, and tubing means 64 connects the dental tool 60 to the main valve outlet 20 (FIG. 4), whereby the tool 60 is powered by the fluid when the main valve 14 is open, and the main valve 14 is closed when the tool 60 is stored in the recess 56.

Figure 8:
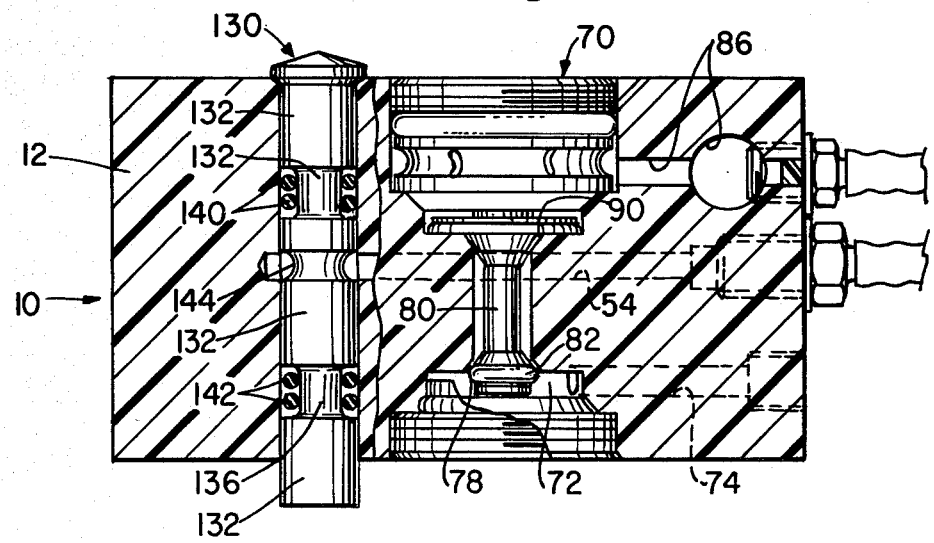
FIG. 8 is a sectional view taken substantially along the line 8—8 of FIG. 4 and looking in the direction of the arrows.

The apparatus further comprises a water valve 70 (FIGS. 4 and 8) mounted in the housing means 12 in spaced-apart relation to the main valve 14 and the sensing means 16. The water valve 70 is formed with a water chamber 72 having a water inlet port 74 and a water outlet port 76. The water valve 70 comprises a water valve seat 78 and a water valve member 80 cooperating therewith.

The water valve member 80 is movable between a closed position in which an O-ring 82 engages the water valve seat 78 and blocks flow of water from the water inlet 74 to the water outlet 78 and an open position (shown in FIG. 4) in which it is spaced apart from the water valve seat 78 and enables such flow.

Figure 6:
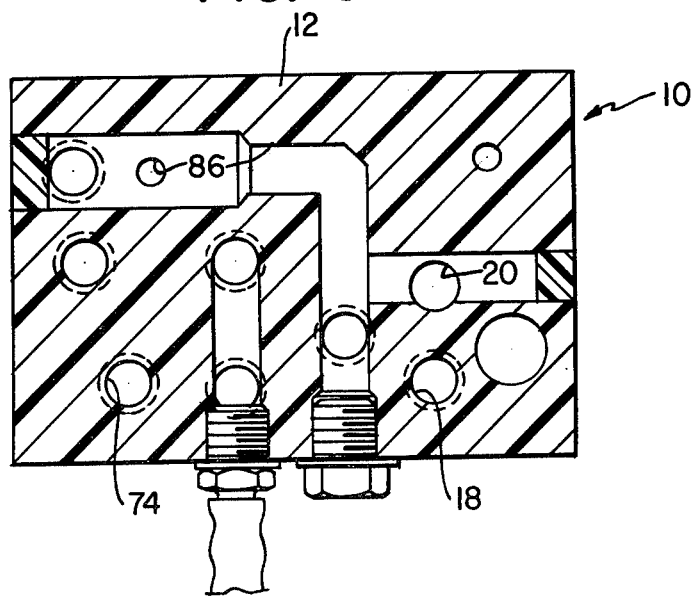
FIG. 6 is a sectional view taken substantially along the line 6—6 of FIG. 2 and looking in the direction of the arrows.

AND-gate means (FIG. 9) is mounted downstream of the outlet 20 (i.e., the outlet for the main valve 14) and in fluid communication therewith. Fluid passage means 86 (FIGS. 6 and 8) provides communication between the AND-gate means and the water valve means 70.

Means is provided for actuating the AND-gate means, whereby a portion of the fluid passing through the outlet 20 (FIG. 4) is bled through the fluid passage means 86 to the water valve member 80 and applies a force urging the water valve member 80 to the open position shown in FIG. 4. The net cross-sectional area of the water valve member 80 exposed to the fluid bled from the AND-gate exceeds the net cross-sectional area of the water valve member exposed to the water chamber 72. The water valve member 80 is identical to the valve member 24 except that the valve member 80 lacks the central longitudinal passage 34, 36 of the valve member 24. Consequently, the same considerations apply in calculating the net cross-sectional area of this valve member exposed to the pilot air pressure above and the water pressure below. Because of the differential cross-sectional areas, a relatively low pressure above the water valve member 80 is sufficient to force it to the open position against a larger water pressure below the valve member 80.

The water valve 70 further comprises a second water valve seat 90. The water valve member 80 is spaced apart from the second water valve seat 90 when the water valve 80 is closed and engages the second water valve seat 90 when the water valve 80 is open. Water passing between the water valve member 80 and the first-named water valve seat 78 when the water valve 70 is open can exit through the water valve outlet 76 but is prevented from counteracting the valve-opening force applied by the fluid bled from the AND-gate means (FIG. 9).

As FIG. 9 shows, the AND-gate means comprises a valve member 100 normally venting bleeding of a portion of the fluid passing through from the primary air chamber outlet 20. Control means including air from a pedal control, which is connected to the air source 52 and can be operated for example by the dentist's left foot, is provided for selectively applying air pressure to the valve member 100. The valve member 100 is in communication with a line 112 (FIG. 9) and moves upward as seen in FIG. 9 in response to this air pressure, whereby an O-ring 102 becomes unseated from a valve seat 104 to effect such bleeding.

The valve member 100 has a reduced diameter shaft fitting within a bore 106 so that air from the primary air chamber outlet 20 can pass around the valve member 100 without substantial obstruction. This provides the drive air to the dental handpiece turbine.

The valve member 100 can be restored to its closed position shown in FIG. 9 by gravity, or the movement of the valve member towards the closed position can be assisted by a spring (not shown) or other biasing means.

Needle valve means 114 (FIGS. 1–5 and 7) controls the rate of water flow when the water valve 70 is open. The needle valve 114 includes a control knob 116 attached to a shaft 118 which is inserted by means of threads 120 into the housing 12 and includes a needle portion 122 adapted to create an adjustable orifice 124 communicating with the water supply line 126 (FIGS. 4 and 5) for the dental tool 60.

The apparatus also includes lockout means 130 (FIGS. 1, 2, 3 and 8) for selectively interrupting the air stream in the passage 54 and thus ensuring that the main valve 14 remains closed. The lockout means 130 includes a piston 132 having reduced portions 134 and 136 in which are respectively mounted O-rings 140 and 142. With the lockout means 130 in the lower position shown for example in FIG. 8, a reduced diameter portion 144 is aligned with the air passage 54 and permits flow of air through this passage. When the lockout means 130 is raised to the position of FIG. 1, a large diameter portion of the shaft 132 (see, e.g., FIG. 8) blocks the passage 54 and prevents a jet of air from flexing the diaphragm 32 even when the dental tool 60 is withdrawn from the recess 56.

The lockout means 130 is thus a two-position manually-operable valve, the valve in one position blocking the passage 54 and in the other position unblocking the air passage 54.

Figure 7:
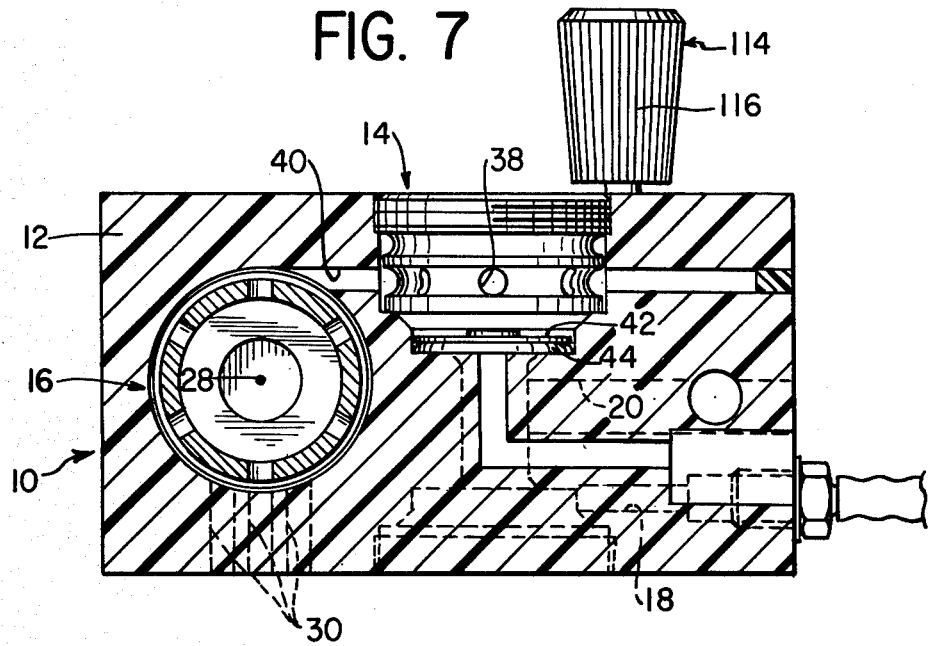
FIG. 7 is a sectional view taken substantially along the discontinuous line 7—7 of FIG. 4 and looking in the direction of the arrows.

The air valve 14, sensing means 16 and water valve 70 employ conanda-type baffle plates for directing air flow. For example, the air escaping through the restricted orifice 36 (FIG. 4) flows radially out through the apertures 38 (FIG. 4) and through the passage 40 (FIG. 7). The air then flows circumferentially around a conanda baffle plate and radially in through apertures 29. It then flows axially through the passage 28 (FIG. 3) and out the exhaust ports 30 (FIGS. 3 and 7).

Thus there is provided in accordance with the invention a novel and highly effective fluidic block whereby many power and control functions that have heretofore required bulky, expensive and complicated equipment can be performed by equipment that is compact, inexpensive, and simple. Many modifications of the preferred embodiments of the invention disclosed above will readily occur to those skilled in the art upon considering this disclosure. Accordingly, the invention is to be construed as including all such embodiments within the scope of the appended claims.

What is claimed is:

1. Apparatus comprising housing means, a main valve mounted in said housing means, and separate sensing means mounted in said housing means in spaced-apart relation to said main valve, said main valve being formed with a main valve chamber having an inlet port and an outlet port and said main valve comprising a valve seat and a valve member cooperating therewith, said valve member being movable between a closed position in which it engages said seat and blocks flow of fluid from said inlet to said outlet and an open position in which it is spaced apart from said seat and enables such flow, said sensing means including an exhaust to the atmosphere and exhaust shut-off means actuable for closing said exhaust, said housing and main valve being formed with a passage enabling restricted leakage of fluid from said main chamber to said sensing means for exhaust to the atmosphere when said valve member is in said closed position, said leakage fluid being in communication with said valve member and when pressurized applying a force urging said valve member to said open position, the net cross-sectional area of said valve member exposed to said leakage fluid exceeding the net cross-sectional area of said valve member exposed to said fluid in said main chamber;

whereby introduction of pressurized fluid into said main chamber coupled with actuation of said exhaust shut-off means builds up the pressure of said leakage fluid and opens said main valve.

2. Apparatus according to claim 1 wherein said passage extends the length of said valve member.

3. Apparatus according to claim 1 wherein said main valve further comprises a second valve seat, said valve member being spaced apart from said second valve seat when said main valve is closed and engaging said second valve seat when said main valve is open, whereby fluid passing between said valve member and said first-named valve seat when said main valve is open can exit through said outlet but is prevented from counteracting the valve-opening force applied by said leakage fluid.

4. Apparatus according to claim 1 wherein said exhaust shut-off means comprises a flexible diaphragm movable between a normal position in which it leaves said exhaust open and a flexed position in which it closes said exhaust.

5. Apparatus according to claim 4 further comprising means for flexing said diaphragm.

6. Apparatus according to claim 5 wherein said means for flexing said diaphragm comprises means for directing an air stream against said diaphragm.

7. Apparatus according to claim 6 wherein said means for directing an air stream against said diaphragm comprises a source of compressed air and an air passage extending through said housing and communicating with said source.

8. Apparatus according to claim 7 wherein said housing is formed with a recess and said air passage communicates with said recess, whereby an obstruction placed in said recess interrupts said air stream and prevents said air stream from flexing said diaphragm.

9. Apparatus according to claim 8 further comprising a fluid-powered dental tool adapted to be stored in said recess and tubing means connecting said tool to said outlet, whereby said tool is powered by said fluid when said main valve is open and said main valve is closed when said tool is stored in said recess.

10. Apparatus according to claim 1 further comprising a water valve mounted in said housing means in spaced-apart relation to said main valve and said sensing means, said water valve being formed with a water chamber having a water inlet port and a water outlet port and said water valve comprising a water valve seat and a water valve member cooperating therewith, said water valve member being movable between a closed position in which it engages said water valve seat and blocks flow of water from said water inlet to said water outlet and an open position in which it is spaced apart from said water valve seat and enables such flow, AND-gate means mounted downstream of said first-named outlet and in fluid communication therewith, fluid passage means in said housing providing communication between said AND-gate means and said water valve means, means actuating said AND-gate means, whereby a portion of the fluid passing through said outlet is bled through said fluid passage means to said water valve member and applies a force urging said water valve member to the open position, the net cross-sectional area of said water valve member exposed to said fluid bled from said AND-gate means exceeding the net cross-sectional area of said water valve member exposed to said water chamber, whereby actuation of said AND-gate means when said main valve is open opens said water valve.

11. Apparatus according to claim 10 wherein said water valve further comprises a second water valve seat, said water valve member being spaced apart from said second water valve seat when said water valve is closed and engaging said second water valve seat when said water valve is open, whereby water passing between said water valve member and said first-named water valve seat when said water valve is open can exit through said water valve outlet but is prevented from counteracting the valve-opening force applied by said fluid bled from said AND-gate means.

12. Apparatus according to claim 10 wherein said AND-gate means comprises a valve member normally preventing bleeding of said portion of the fluid passing through said outlet, and control means for selectively applying air pressure to said last-named valve member, said last-named valve member moving in response thereto to effect said bleeding.

13. Apparatus according to claim 10 further comprising needle valve means for controlling the rate of water flow when said water valve is open.

14. Apparatus according to claim 8 further comprising lockout means mounted in said housing for selectively interrupting said air stream and thus selectively ensuring that said main valve remains closed.

15. Apparatus according to claim 14 wherein said lockout means comprises a two-position manually-operable valve, said valve in one position blocking said air passage and in the other position unblocking said air passage.

16. Apparatus according to claim 10 further comprising coanda baffle plate means for controlling air flow in said main valve, said sensing means, and said water valve.

* * * * *